United States Patent [19]

Mochizuki et al.

[11] 4,155,683
[45] May 22, 1979

[54] SYSTEM FOR AND A METHOD OF PROVIDING A LIQUID CHROMATOGRAPHY ELUENT

[75] Inventors: Koichi Mochizuki, Tsushima; Mitsuo Watanabe, Ama; Mueno Saito, Tama, all of Japan

[73] Assignee: Japan Spectroscopic Co., Ltd., Hachioji, Japan

[21] Appl. No.: 792,985

[22] Filed: May 2, 1977

[30] Foreign Application Priority Data

May 1, 1976 [JP] Japan ................................. 51/50380

[51] Int. Cl.² .......................... F04B 1/12; B67D 5/56; B67D 5/00
[52] U.S. Cl. ..................................... 417/269; 222/14; 222/135
[58] Field of Search ...................... 73/61.1 C; 417/269, 417/426–429, 442; 222/14, 135, 136, 71, 144.5

[56] References Cited

U.S. PATENT DOCUMENTS

| 29,454 | 10/1977 | Ashmead | 73/61.1 C |
| 2,215,827 | 9/1940 | Ditto | 417/428 |
| 3,144,831 | 8/1964 | Pickels et al. | 417/429 |
| 3,827,830 | 8/1974 | Van Horn | 417/390 |
| 3,976,400 | 8/1976 | Major | 417/429 |
| 3,985,021 | 10/1976 | Achener | 73/61.1 C |
| 4,019,652 | 4/1977 | Suh et al. | 222/1 |

Primary Examiner—William L. Freeh
Attorney, Agent, or Firm—Browdy and Neimark

[57] ABSTRACT

A system for and a method of providing an eluent composed of two different kinds of liquids being mixed at a set concentration and further a time varying concentration or mixing ratio, comprising (a) a step for transferring each of the two liquids by sucking under low-pulsation to on-off valves; (b) a step for periodically controlling the operation of the on-off valves; (c) a step for controlling the amount of each liquid supplied to the mixing region during each period of valve operation; (d) a step for substantially sucking the eluent formed by the above steps in the mixing region for discharging or supplying the same under the same low-pulsation, whereby a mixing of the two liquids under an atmospheric or a low constant pressure, can be effected and a supply of an eluent having a precisely controlled time varying concentration of each liquid can also be effected, and a system for providing such an eluent. Further a system for preparing such an eluent composed of more than two different kinds of liquids can be provided.

7 Claims, 8 Drawing Figures

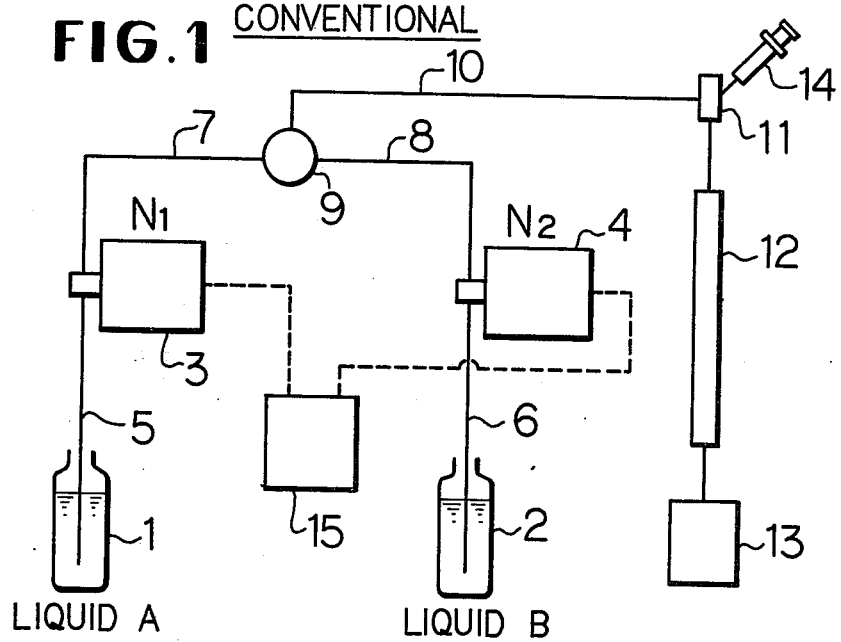
FIG. 1 CONVENTIONAL
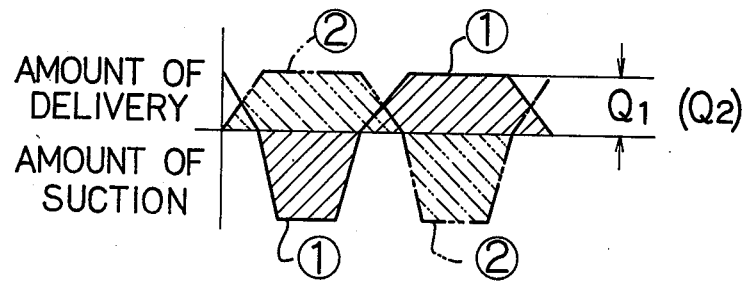
FIG. 2
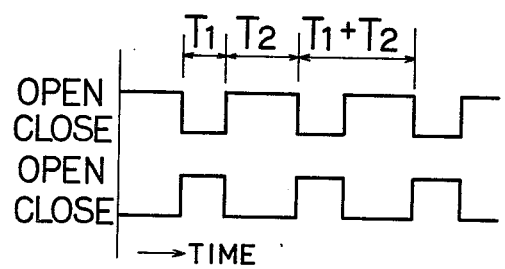
FIG. 5 (a)
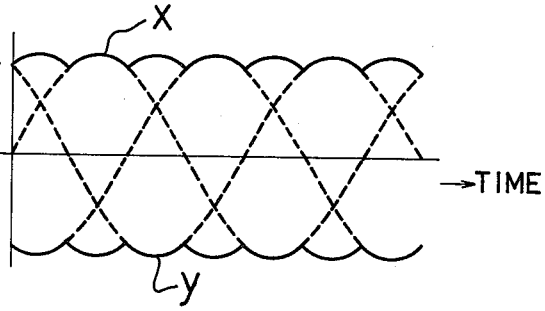
(b)

SYSTEM FOR AND A METHOD OF PROVIDING A LIQUID CHROMATOGRAPHY ELUENT

BACKGROUND OF THE INVENTION

This invention relates to a system for the liquid chromatography as a separating or analysing instrument, commonly used in the chemical, biological, medical, and the like science fields, and a liquid supplying method employed for supplying an eluent for the abovementioned purpose. More particularly it relates to an eluent preparing and pumping system for use in a so-called high speed chromatography apparatus; in other words, to a provision of a novel pumping system, enabling a non-pulsating sucking of liquids and perfect mixing thereof as the most important factors, and an eluent supplying method for that purpose.

More specifically still, it relates to a method and system for producing an eluent having a time varying concentration of different liquids.

In general, the simplest elution system, used for example in a liquid-chromatographic column, supplies an eluent comprising a single liquid to the column. In many instances, however, this single liquid is not effective in removing all of the desired material from the column, and a second liquid must subsequently be supplied. Alternately, an eluent having a set concentration of the two liquids is used. More than two liquids can be and have been used, but for convenience in describing the prior art and the present invention, the discussion is limited in what follows to a system using two liquids which are labelled as liquid A and liquid B, in general. Switching liquids in mid-operation and the use of a mixture of liquids have not been favored procedurally, and there has been a recent tendency to gradient elution systems. In gradient elution, the initial eluent contains a set concentration of the liquids (usually 100% of A and none of B), and this concentration is slowly altered, through intermediate concentration, to a second set concentration of the liquids (usually none of A and 100% of B).

Required conditions for the pumping system in a liquid chromatography used in such a gradient elution system are: (1) mixing of liquids at a precise and freely variable concentration with a gradual and stepless gradient: (2) constant flow rate especially in an almost non-pulsating state, referred to hereafter as low-pulsation; (3) resistance against high pressure, that is, capacity of attaining a considerably high flowing rate even inside a small-diametered column, etc.

Conventional apparatuses, as one of the representative example thereof FIG. 1 being shown, have been in an unsatisfactory state from the abovementioned viewpoint. In this apparatus, each liquid A and B filled in each independent liquid source container (hereinafter simply called liquid container) 1 and 2 is sucked into, by means of each pump 3 and 4, each suction pipe or tube 5 and 6, and then sent into a mixing-and-stirring chamber (hereinafter simply called mixing chamber) through each discharge pipe 7 and 8, and finally led, through a liquid supply pipe 10, a sample injecting pipe 11, and a column 12, into a detector 13. The sample is timely or at a suitable interval injected, at a sample injecting pipe 11 disposed on the way of the liquid supply pipe 10 by means of a sample injector 14. Both liquids A and B are respectively flow-controlled by a flow-rate programmer 15, at a set flow rate, into a mixture of desired concentration, and further formed into an eluent with a time varying concentration. And the pair of pumps 3 and 4 are varied, in the course of the above operation, respectively in the number of rotation for varying the ratio of discharge amount of each liquid, thereby timewise varying the ratio of the discharge amount.

This type method and apparatus therefor is, however, still not free from some disadvantages: one pump is required for each liquid; the pump used therein cannot be said to be a low-pulsation pump; viscosity, compressibility, vapor pressure, etc., peculiar to each liquid tend to hinder a precise proportioning of the number of pump rotations to the mixing ratio of the liquids. Difficulty of preparing an eluent having a precise mixing ratio of A and B liquids in this programming system may be said to be a decisive disadvantage to a gradient elution system which essentially requires a precise controlling of the liquids concentration.

Furthermore, another elution system was made public in Toku-Ko-Sho No. 50-19959 in Japan as follows:

An elution system comprising:
(a) a source of first liquid;
(b) a source of second liquid;
(c) first liquid supply means connected to said source of first liquid;
(d) second liquid supply means connected to said source of second liquid;
(e) proportioning means comprising a mixing region, valving means connected to said mixing region, and programming means connected to said valving means, said valving means having at least two operative portions, a first operative portion connected between said first liquid supply means and said mixing region in a manner such as to supply said mixing region with said first liquid when said first operative portion is activated and a second liquid supply means and said mixing region in a manner such as to supply said mixing region with said second liquid when said second operative portion is activated, said programming means being adapted to periodically control the time during which each operative portion of said valving means is activated, said mixing region comprising means to allow a portion of any liquid contained in said mixing region to be removed from said mixing region.

Some disadvantages are still to be pointed out even in this elution system, most of those coming from a fact that each liquid is obliged to be mixed under a high pressure, because the pump is disposed between each liquid container and each valving means for supplying the liquid to the valving means thereby. The mixing of liquids under this high pressure still provides several problems involved therein. In this system, controlling of the liquid supply is carried out by the valving means instead of the conventional method of doing it by the number of pump rotations, which allows a fairly precise mixing ratio between each liquid, to be sure, but still is not free from some deviation from the predetermined program value of the mixing ratio, because of the mixing process under the high pressure. Difference of compressibility of each liquid may be a main cause of the abovementioned deviation, when the mixing is carried out under the condition of high pressure like this. Although the compressibility of liquids is smaller than that of gases, even a slight difference between liquids of this inherently small liquid compressibility can affect the mixing ratio of liquids in the present day precise liquid chromatography which requires a high speed analysis, by flowing the eluent at a high speed into the column, under a high pressure more than 50 Kg/cm² or sometimes over 100 Kg/cm². A minute variation of the mixing ratio of the liquids derived from the difference of the compressibility between liquids can cause an innegligible increasing of analysis errors.

Occurrence of pulsating flow of liquid, which is observed on the outlet or discharge side by dint of a pump disposed in this type of elution system, renders the base line of a chromatogram described in the liquid chromatography unstable. This also provides another problem giving rise to an imprecise or inaccurate quantative analysis.

SUMMARY OF THE INVENTION

The main object of this invention is to provide a system for and a method of providing an eluent composed of liquids of respectively precisely controlled concentration and a pumping system therefor.

Another object of this invention is to provide an eluent wherein each composing liquid is of precisely controlled time varying concentration.

Another important object of this invention is to provide an eluent pumping system which enables each composing liquid to be sucked under a low-pulsation by a suction means, to be mixed, under the normal or atmospheric pressure or a low constant pressure nearby, at a set mixing ratio programmed, and to be sent under a low-pulsation as well as a high pressure condition, by means of specifically or peculiarly designed pump to the chromatographic column.

Still another object of this invention is to provide a method and system for preparing an eluent having a time varying concentration of liquids, in which a single pump is used.

Other objects and features of this invention will be apparent from the following description taken in conjunction with the accompanying drawings and appended claims.

The objects of this invention above described can be attained by a device comprising (a) plurality of liquid source containers for each different liquid; (b) plurality of intake or suction pipes for sucking each liquid from each container; (c) plurality of valving means for blocking and permitting the flow of each liquid sucked by each suction pipe; (d) a programming means for periodically controlling the time required to block or permit the flow of each liquid; (e) a mixing region being connected to each suction pipe; and (f) pump means connected downstream of the mixing region, whereby the pump means enables by means of its operation each liquid to be sucked under low-pulsation from each liquid container, through each suction pipe, into the mixing region, for being mixed therein to form an eluent of predetermined or set mixing ratio, and enables the eluent thus produced to be delivered to the liquid supply pipe leading to the column, under low-pulsation, by the operation of the pump means itself.

As can be easily understood from the above, (a) this invention permits a preparation of an eluent mixed at a precisely set ratio programmed, not being affected by any variation of the mixing ratio due to the difference of compressibility of each liquid, leading to a precise quantitative analysis, because each liquid is sucked under a low-pulsation, flowed into the mixing region by means of valving means alternatively, for being mixed under the atmospheric pressure or a low pressure nearby, at a predetermined ratio; (b) the supply or delivery of the eluent under a low-pulsation into the column makes the base line of a chromatogram stable, leading to the improvement of detection sensitivity; and (c) the disposition of the pump means, for delivering the eluent under high pressure, downstream of the mixing region allows the valving means, the mixing region, the piping, etc., not to be pressure-resistant, which thereby allows a compact and economical design of the analysis apparatus, and also allows to easily deliver the eluent, having a precise mixing ratio of each liquid, to the column under a high pressure more than 50 Kg/cm² or sometimes over 100 Kg/cm².

Furthermore, a continuous suction of the liquids and discharge of the eluent under low-pulsation can be, as later be described, achieved by actuating three or more plunger pump-units in a regular turn and recycling the same operation.

BRIEF DESCRIPTION OF THE DRAWINGS

FIG. 1 is a diagrammatic chart of a conventional system;

FIG. 2 is a graph showing the curves of discharge and suction quantity variation when the pulsation of discharge is eliminated by a conventional dual-plunger type pump;

FIG. 3' is an alternate of FIG. 3;

Identical or related numerals are attached to the members having similar or like functions.

DESCRIPTION OF THE PREFERRED EMBODIMENTS

Figure 3:
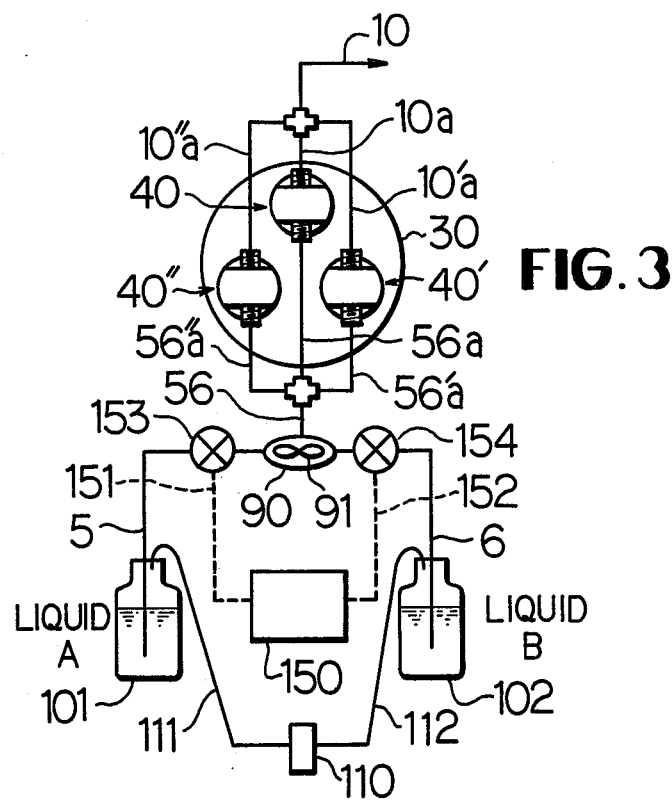
FIG. 3 is a diagrammatic chart of an example or a first embodiment of the pumping system in accordance with this invention.

Referring to FIG. 3, which is an example of the pumping system in accordance with this invention, a process of preparing an eluent composed of two different kinds of Liquids A and B mixed at a predetermined ratio will be described. Numerals 101 and 102 represent respectively a liquid container for liquids A and B, which may be either an open or closed container with a plug. It is, however, preferable to keep this pair of containers under a pre-pressured state, upon sealing both 101, 102, connecting them respectively to a low-air-pressured accumulated chamber 110 through pipes or tubes 111, 112. Although an air pressure in the range of 0.1–0.3 Kg/cm² (guage) is sufficient, a high pressure may be acceptable so long as it does not affect the suction by a pump 30 of the liquids A and B. That pre-pressuring of the container may be contributable to the prevention of pressure variation of the liquids due to viscosity thereof, etc., or producing of gases (due to evaporation of gases such as the air dissolved in the liquids), within the suction pipes 5, 6 and thereby to the restraining of the flow amount variation of the liquids.

In a particular event of high speed liquid-chromatographic analysis, requiring rapid preparation of the eluent for sending or delivering the same at a high speed and under a high pressure to the column, wherein large amount of liquids A and B must be sucked by driving the pump 30 at a high speed, it is recommendable to adopt the pre-pressuring process. Suction pipes 5, 6 join or flow into a mixing-and-stirring chamber (hereinafter simply called mixing chamber) 90 by way of each solenoid valve 153 and 154, which is respectively connected to a flow controlling programmer (hereinafter simply called programmer) 150 with an electric wire 151 and 152 for being programmatically controlled.

Figure 5:
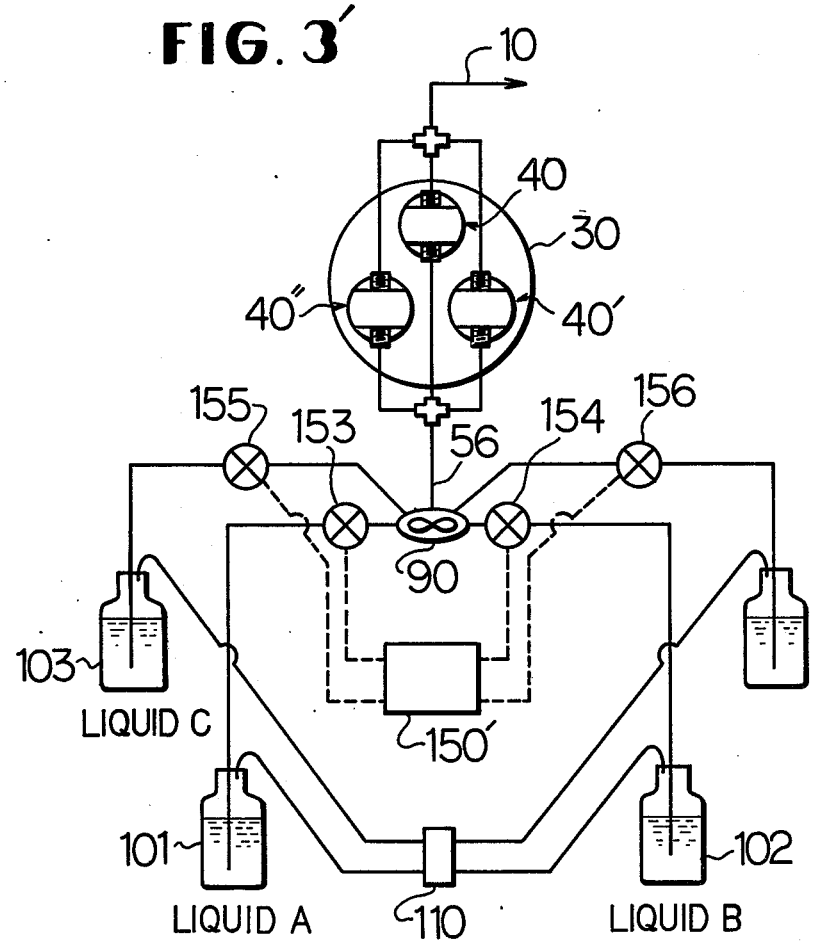
FIG. 5 (a) is a graph for explaining the opening and closing or on-off conditions of the solenoid valves 153 and 154; and (b) is a graph for showing the discharge and suction quantity variation of the pump assembly shown in FIG. 4.

An example, shown in FIG. 5 (a), illustrates that during the time $T_1$ the solenoid valve 153 is open while the solenoid valve 154 is closed, and during the time $T_2$ the former is, on the contrary, closed and the latter is open. The ratio of $T_1$ to $T_2$ corresponds to the mixing ratio of liquid A to liquid B. The total amount of liquids A and B supplied to the mixing chamber 90 during the total time of $T_1+T_2$ is always kept constant, and the ratio of $T_1/T_2$ may be gradually varied from the desired maximum, that is to say, a gradual timewise varying of the liquids concentration, a gradient elution, becomes feasible.

The two liquids A and B which have been stirred-and-mixed substantially homogeneously, in the mixing chamber 90 provided with stirring means 91 for example a rotary blade or blades, will be sucked through a sucking pipe 56 into the pump 30. As to the construction of the pump 30, FIG. 4 should be referred to. Three plungers 35, which are disposed on a same circumference with 120° phasic angle difference to each other, contact with respective ball-ends on a swash plate 32 which is rotatably retained in a housing 31, and are respectively reciprocable in the axial direction. The swash plate 32 is a slantly cut-off column (or an inclined disc may be used), and the surface 32a is slant against the axis of the pump with a predetermined angle, on the side where the plungers 35 contact, to make the plungers 35 axially reciprocate. The swash plate 32 is driven by a variable speed motor 100, which is secured to the housing 31, for being rotated as a unit with a rotatable shaft 33 sustained by a bearing 34. Reference numeral 45 represents a speed changing mechanism. Each plunger 35, provided with a spring 36 and a sealing member 37, reciprocates in and out of a liquid chamber 40a in a pump unit 40 secured to the housing 31, which liquid chamber is provided with a suction valve 38 at a port connected to a suction pipe 56a and a delivery valve 39 at another port connected to a liquid supply pipe 10a. Each of three suction pipes 56a, 56'a, 56"a of the three pump units join into the suction pipe 56, and each of three pump liquid delivery pipes 10a, 10'a, and 10"a join into a liquid supply pipe 10, which is connected to the column, although not shown, of the liquid chromatography just like in FIG. 1. In response to the rotation of the swash plate 32, which is driven by the variable speed motor 100, each plunger 35, 35', and 35" of each pumping unit 40, 40', and 40" will be respectively reciprocated in the axial direction in turn, that is to say, the three pumping units in FIG. 3 will be actuated in the clockwise turn, 40, 40', and 40", or counterclockwise turn, 40", 40', and 40, causing the suction and discharge. The eluent formed in the mixing chamber 90 is sucked through the suction pipes 56a, 56'a, and 56"a, and discharged through the liquid delivery pipes 10a, 10'a, and 10"a, and the flow of the eluent through the main suction pipe 56 can be continuous and the flow of the eluent through the main supply pipe 10 can also be continuous. The suction and the delivery by each plunger 35 is what is shown in FIG. 5 (b), and the curves of the total discharge volume x and the total suction volume y are, as is well known, the sum of three sine curves, in which the maximum flow variation due to pulsation is very small. A single unit including such plungers is capable of keeping the pulsation of the suction as well as discharge extremely low, which means that the variation of the mixing ratio due to the pulsation can be so effectively restrained that the exact maintenance of the program-controlled pulsation cycle of the pump flow rate and the on-off cycle of the solenoid valves, makes it extremely easy to homogenize the eluent to an extent fully adapted to the timewise variation of the mixing ratio in a normal gradient elution in which the concentration of both liquids are timewise varied. For instance, at an assumption of the pump pulsation cycle being 2 seconds and the on-off cycle $(T_1+T_2)$ of the solenoid valves being 3 seconds, a perfect homogenization of liquids at a set mixing ratio within a cycle of 6 seconds, the least common multiple of 2 and 3, can be attained, which cycle is a duration of time wherein a normal stirrer can achieve a liquid homogenization easily and perfectly.

Employing a conventional dual-plunger type pump, in place of the pump 30, showed an unsatisfactory result, because it was utterly impossible, regardless of a good achievement on the delivery side, to hold the liquid flowing down to a non-pulsating state on the suction side. In order to satisfy the prerequisite necessary for the eluent system, keeping the sum of the sucked liquids $(Q_1+Q_2)$ into the mixing chamber 90—liquid amount flowing in a unit of time—constant in amount, the conventional type dual-plungered pump is obliged to sacrifice the non-pulsation of the suction side, even if it is possible to keep the discharge non-pulsative.

This can be explained by the FIG. 2, in which ① is a discharge-suction curve of a first plunger and ② is that of a second plunger. Making the cam configuration for each plunger adapted to the repetition of such a suction-discharge is possible. In this instance, however, the suction volume (hatched area on the suction side) and the discharge volume (hatched area on the discharge side) must be equal in each case of ① and ② and moreover, it is required that the sum of the discharge amount in ① and ② must be a certain constant amount $Q_1$ or $Q_2$. For satisfying this condition the sum of ① and ② on the suction side cannot illustrate a continuously smooth curve, but shows, as can be seen in FIG. 2, an intermittent or irregular curve, that is an intermittent suction. In other words, to make the combined discharge rate constant, the combined suction rate cannot be constant.

As for the mixing region in this invention for mixing the liquids A and B or more, any type of mixing region is allowable so long as it is capable of forming an eluent composed of two or more kinds of liquids. In one embodiment the mixing region can be a separate mixing chamber with a volume substantially larger than the maximum volume of liquid entering the mixing region during the period when either operative portion of the valving means is activated, and the chamber can be provided with some means to thoroughly mix the liquids in the chamber so that the mixture is homogenous throughout the chamber.

Figure 6:
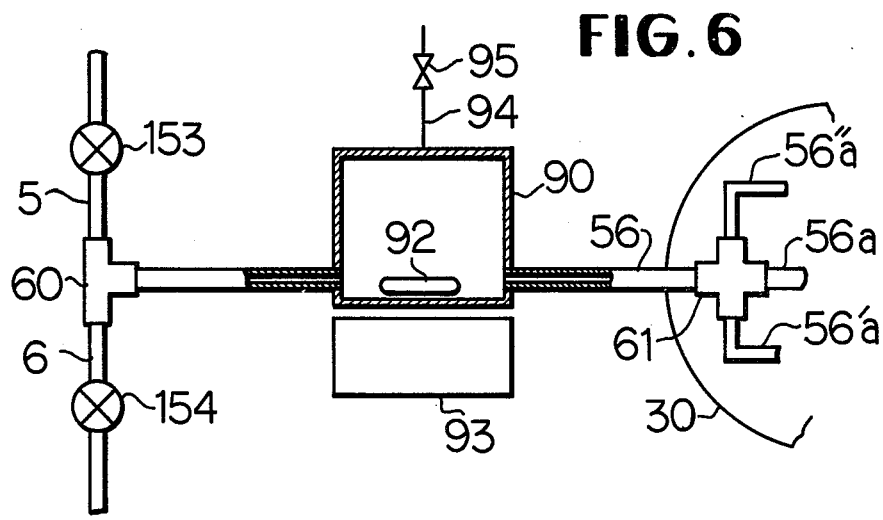
FIG. 6 is a schematic view, partially broken away, of a second embodiment of the mixing region employed in this invention.

In order to turn each liquid, sucked into the mixing region, into a homogeneously mixed eluent, provision of a mixing chamber including a suitable stirring means, as illustrated in FIG. 3, is recommended. As another embodiment for showing such type of mixing chamber, FIG. 6 will be described. A mixing chamber 90 is provided on the way of suction pipe 56. The upstream side end of the suction pipe is connected with a three way joint or connector 60 to the suction pipes 5, 6, and the downstream side end of which is connected with a cross joint to each suction pipes 56a, 56'a, and 56"a of each pumping unit. The volume or capacity of the mixing chamber 90 is made substantialy larger, for forming an eluent of predetermined mixing ratio of A to B, than the sum of the liquids A and B which are sucked into by the on-off of the solenoid valves 153, 154. The mixing chamber 90 is provided with, in addition, a vent means of pipe 94, communicating with the inside thereof, on the top thereof. And the vent pipe 94 has a valve 95, which is capable of trapping a small amount of gas, which may be produced in the chamber 90 due to the on-off operation of the solenoid valves (generally due to evaporation of the air dissolved in the liquids A and B) 153, 154 in the chamber 90 and thereby exhausting it for preventing the variation or fluctuation of the volume of the liquids sucked or discharged owing to the suction of the gas. The chamber 90 is also provided with a magnetic stirrer at the lower portion thereof, a stirring member 92 of which is rotated by a driving mechanism 93 located outside of the chamber for homogeneously mixing the liquids A and B flowed into the mixing chamber 90.

Regarding valving means and programming means, detailed disclosure was made in Toku-Ko-Sho No. 50-19959, a patent publication in Japan, which disclosure can be applicable to this invention, in sucking the liquids A and B at a set or predetermined mixing ratio, by means of employing, in such a sucking process, the invented pump means, and then in flowing them into the mixing region.

Referring to FIG. 3', it should be understood that more than two kinds of liquids, i.e., liquid A, liquid B, liquid C—can be similarly, as in case of FIG. 3, and easily used, that is, mixing in the chamber 90 by the flow controlling programmer 150' which is substantially same as the programmer 150 but capable of time controlling for more than two valves including 155, 156— while the total sum of the suction of liquids is kept always constant. It is also desirable to provide a common accumulator chamber 110 from which a common low pressure is applied to every liquid container 101, 102, 103—. This low back pressure may be of help to supply the mixed eluent to the suction of the pump 30 under a super charging condition.

Referring to FIG. 3 or 3' illustrating a typical embodiment of the present invention which features in a system combining a pump unit with a same low pulsation in both suction and delivery with a low pressure mixing device (or a mixing device disposed in the suction line of the pump), it can be clearly understood that the present invention enables one to prepare a gradient elution composed of more than two liquids very easily without trouble while keeping an extremely precise mixing ratio among the liquids.

Figure 4:
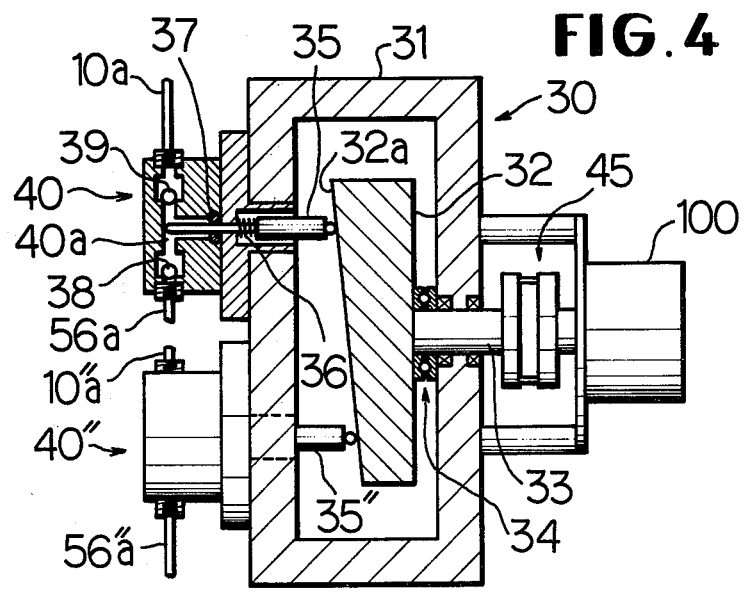
FIG. 4 is an enlarged side view of the pumping assembly shown in FIG. 3, partically in section, for detailed explanation.
Figure 7:
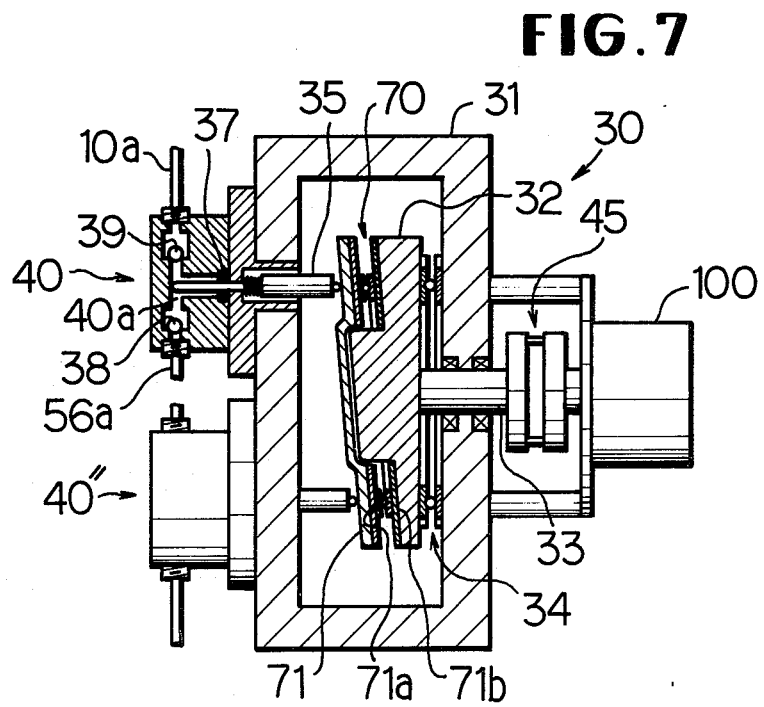
FIG. 7 is an enlarged side view, similar to FIG. 4, of a second embodiment of the pump means employed in this invention.

Referring to FIG. 7, which is similar in outline to and corresponds to FIG. 4, except only in the construction of the swash plate 32, another embodiment concerning the pump means of this invention will be disclosed.

In this swash plate 32, a circumferentially cut away portion of a predetermined width is provided on the surface, on which the tip of the plunger 35 contacts; a ball (or roller) thrust bearing 70 is disposed in such annular cut away or stepped portion. A circular plate 71, being almost the same in size as the swash plate 32, is placed in such a manner as to be sandwiched between the ball thrust bearing 70 and the tip of the plunger 35, which plate 71 is not secured to the swash plate 32 but is movable in respect thereto. The presence of the ball thrust bearing 70, which comprises balls 71a and a retainer 71b, restrains the rotation of the circular plate 71 nearly to zero while the swash plate 32 is rotated by the variable speed motor 100. This function of the rotatable bearing 70 and plate 71 means that the plunger 35 receives substantially only an axial displacement or movement and the same is almost free from the effects of the torque which may be caused by the rotation of the swash plate 32, because there is substantially no relative rotation between each plunger and the plate 71. It will further contribute to the prevention of wearing, damage, etc., of the plunger 35 thereby to the improvement of the pumping function, that is, suction or discharge at a predetermined rate.

Summing up the abovementioned description, essential effects of this invention will now be digested.

A system combining a pump unit having a same low pulsation in both suction and delivery with a low pressure mixing device on the suction side of the pump enables the followings:

(a) A gradient elution is very easily performed without trouble while keeping an extremely precise mixing ratio of the liquids, even among more than two liquids.

(b) The mixing region needs only being resistant to low pressure, while contributes not only to enhancing accuracy of analysis but also to the manufacturing cost reduction and the decrease of liquid leakage chance and thereby to the maintenance of the precise mixing ratio.

(c) A flexible controlling of the concentration of each liquid as well as of the speed of concentration variation is possible (by controlling the speed of the motor).

(d) Reduction of the number of pumps required.

(e) Stabilisation of base line of the chromatogram and the improvement of the detection sensitivity therethrough.

While the invention has been described in conjunction with certain embodiments thereof it is to be understood that various changes and modifications may be made without departing from the spirit and scope of the invention.

What is claimed is:

1. A system for preparing a liquid chromatography eluent comprising:
   (a) a plurality of liquid source containers for respectively containing each of different liquids;
   (b) a plurality of suction pipes for respectively sucking said each liquid in said liquid source containers;
   (c) valving means for respectively blocking or pemitting the flow of said each liquid sucked by said suction pipes;
   (d) a programming means connected to said valving means for effecting the flow of said each liquid;
   (e) a mixing region connected to each of said suction pipes; and
   (f) a pump unit connected downstream of said mixing region, whereby said pump unit sucks, through the operation thereof, said each liquid under low pulsation from said each liquid source container through said each suction pipe into said mixing region, and discharges, upon having formed an eluent of desired mixing ratio, said eluent being delivered under the identical low pulsation with said suction pulsation, by means of the operation thereof, into the liquid supply pipe leading to the column, wherein said pump unit is of the swash plate type and comprises a rotating slanting flat surface swash plate with at least three pumping chambers having respective pumping plungers disposed parallel to each other in the axial direction of the plate at the same radial distance from the rotational axis at equal circumferential angles from each other and being drivingly coupled to said swash plate, and means for imparting a predetermined pre-pressure to each of said liquid source containers.

2. A system as set forth in claim 1, wherein a rotatable thrust bearing and a circular plate are disposed between said swash plate and said plungers for preventing the torque of said swash plate from being transmitted to said plungers.

3. A system as set forth in claim 1, wherein said pre-pressure is in the range from 0.1 to 0.3 $Kg/cm^2$ (gauge pressure).

4. A system as set forth in claim 1, wherein said valving means comprises separate on-off valves adapted to each of said suction pipes one said valves being opened and others of said valves being closed.

5. A system as set forth in claim 4, wherein said on-off valves are solenoid valves.

6. A system as set forth in claim 1, wherein said mixing region comprises a mixing chamber having a volume substantially larger than the maximum volume of liquid entering said mixing chamber during the period when either operative portion of said valving means is activated.

7. A system as set forth in claim 6, wherein said mixing chamber is provided with a vent means and a magnetic stirring means.

* * * * *